US009442096B2

(12) United States Patent
Fujiwara et al.

(10) Patent No.: US 9,442,096 B2
(45) Date of Patent: Sep. 13, 2016

(54) ULTRASONIC TESTING APPARATUS FOR PIPE OR TUBE END PORTION AND METHOD OF SETTING INITIAL POSITION OF PROBE HOLDER

(71) Applicants: Kenji Fujiwara, Osaka (JP); Hiroshi Kubota, Osaka (JP); Tomoyuki Obata, Osaka (JP); Masaki Yamano, Osaka (JP)

(72) Inventors: Kenji Fujiwara, Osaka (JP); Hiroshi Kubota, Osaka (JP); Tomoyuki Obata, Osaka (JP); Masaki Yamano, Osaka (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 778 days.

(21) Appl. No.: 13/654,749

(22) Filed: Oct. 18, 2012

(65) Prior Publication Data

US 2013/0276540 A1    Oct. 24, 2013

Related U.S. Application Data

(63) Continuation of application No. PCT/JP2011/069908, filed on Sep. 1, 2011.

(30) Foreign Application Priority Data

Sep. 9, 2010    (JP) ................................ 2010-201606

(51) Int. Cl.
*G01N 29/24*    (2006.01)
*G01N 29/22*    (2006.01)
*G01N 29/04*    (2006.01)
(Continued)

(52) U.S. Cl.
CPC ............ *G01N 29/22* (2013.01); *G01N 29/043* (2013.01); *G01N 29/225* (2013.01); *G01N 29/275* (2013.01); *G01N 29/28* (2013.01); *G01N 2291/056* (2013.01); *G01N 2291/2634* (2013.01); *Y10T 29/49* (2015.01)

(58) Field of Classification Search
CPC ............... G01N 2291/2634; G01N 2291/044; G01N 29/265; G01N 29/28; G01N 29/225
USPC .................................................... 73/622, 644
See application file for complete search history.

(56) References Cited

U.S. PATENT DOCUMENTS 3,183,709 A * 5/1965 Rankin et al. ................... 73/642
3,416,364 A * 12/1968 Wycherley et al. ............. 73/609
(Continued)

FOREIGN PATENT DOCUMENTS

DE  10 2007 039326    2/2009
GB  2 139 353    11/1984
(Continued)

*Primary Examiner* — Hezron E Williams
*Assistant Examiner* — Nashmiya Fayyaz
(74) *Attorney, Agent, or Firm* — Clark & Brody

(57) ABSTRACT

An ultrasonic testing apparatus includes an ultrasonic probe disposed under an end portion of a pipe laid in the horizontal direction to face the pipe end portion. The probe transmits ultrasonic waves to the end portion of the pipe and receives the ultrasonic waves therefrom. A probe holder housing the probe includes a coupling medium reserver part which surrounds a space between the probe and the end portion of the pipe to contain a coupling medium W. The coupling medium reserver part includes a part body 21 into which the coupling medium is supplied; an annular bellows part, which is attached to the upper side of the part body to internally communicate with the part body, and an annular spacer 23 attached to the upper side of the bellows part, the upper surface of the annular spacer being a flat horizontal surface.

7 Claims, 9 Drawing Sheets

(51) Int. Cl.
  *G01N 29/28* (2006.01)
  *G01N 29/275* (2006.01)

(56) References Cited

U.S. PATENT DOCUMENTS

| | | | |
|---|---|---|---|
| 4,976,149 A * | 12/1990 | Ichikawa | B21B 38/12 367/104 |
| 6,935,178 B2 * | 8/2005 | Prause | 73/622 |
| 8,387,462 B2 * | 3/2013 | Yamano et al. | 73/632 |
| 8,667,847 B2 * | 3/2014 | Fujiwara et al. | 73/644 |

FOREIGN PATENT DOCUMENTS

| | | |
|---|---|---|
| JP | 56-40756 | 4/1981 |
| JP | 59-221663 | 12/1984 |
| JP | 60-29278 | 2/1985 |
| JP | 06-502914 | 3/1994 |
| JP | 09-325133 | 12/1997 |
| JP | 11-2627 | 1/1999 |
| JP | 2001-116729 | 4/2001 |
| JP | 2001-296281 | 10/2001 |
| JP | 2003-302279 | 10/2003 |
| JP | 2005-207795 | 8/2005 |
| JP | 2008-139191 | 6/2008 |
| JP | 2010-256339 | 11/2010 |

* cited by examiner

ULTRASONIC TESTING APPARATUS FOR PIPE OR TUBE END PORTION AND METHOD OF SETTING INITIAL POSITION OF PROBE HOLDER

TECHNICAL FIELD

The present invention relates to an apparatus for ultrasonic testing of an end portion of a pipe or tube such as a steel pipe or tube and a method of setting the initial position of a probe holder that the ultrasonic testing apparatus has. More particularly, the present invention relates to an ultrasonic testing apparatus for a pipe or tube end portion, which enables accurate ultrasonic testing by the stable interposition of a coupling medium between the pipe or tube (hereinafter referred to as "pipe" when deemed appropriate) end portion and an ultrasonic probe and a method of setting the initial position of a probe holder that the ultrasonic testing apparatus has.

BACKGROUND ART

An ultrasonic testing method has been employed widely as a nondestructive inspection method for a pipe such as a steel pipe. In the ultrasonic testing method, a coupling medium such as water is interposed between the pipe and an ultrasonic probe, ultrasonic waves transmitted from the ultrasonic probe are applied to the pipe, and the ultrasonic waves reflected by the pipe are received by the ultrasonic probe.

As an ultrasonic testing method in which ultrasonic probe is disposed under a pipe laid in the horizontal direction, there is a publicly known method for ultrasonic testing of a pipe P in which, as shown in FIG. 1, while an ultrasonic probe 1 is immersed in water W stored in a water tank T, the lower surface of the pipe P is immersed partially in the water W, and the pipe P is conveyed in the axial direction thereof and is rotated in the circumferential direction thereof (for example, refer to "Ultrasonic Testing Series (III) Ultrasonic Testing Method for Seamless Steel Pipe" from the Iron and Steel Institute of Japan, Apr. 15, 1988, pp. 95-96).

According to the above-described method, since the water W serving as a coupling medium can be interposed stably between the pipe P and the ultrasonic probe 1, accurate ultrasonic testing can be performed.

In the configuration shown in FIG. 1, unfortunately, the pipe P is supported at least at two points outside the water tank T. The problem, therefore, is that ultrasonic testing cannot be performed on a pipe end portion, where such a two-point support cannot be used, within the water W in the water tank T. Therefore, the configuration shown in FIG. 1 is mainly used in ultrasonic testing of the central portion of pipe except the pipe end portions.

On the other hand, as an ultrasonic testing apparatus for a pipe end portion, there is a publicly known apparatus provided with an ultrasonic probe and a follow-up device, which causes the ultrasonic probe to follow the pipe rotating in the circumferential direction (for example, refer to JP2008-139191A).

In the case where the ultrasonic probe for ultrasonic testing of the pipe end portion is disposed over the pipe laid in the horizontal direction, it is conceivable for example to use a structure that causes coupling medium to flow down between the ultrasonic probe and the pipe end portion. However, the same structure cannot be used in the case where the ultrasonic probe is disposed under the pipe. In the case where the ultrasonic probe for ultrasonic testing of the pipe end portion is disposed under the pipe, it is conceivable for example to use the water tank as shown in FIG. 1 and immerse the support structure and the follow-up device for the pipe into water in the water tank in a certain configuration. Unfortunately, such a configuration may not be practical because it may be complicated and require a strong waterproof structure, which leads to poor maintainability and an increased cost.

DISCLOSURE OF THE INVENTION

The present invention has been made in view of the above-described conventional art, and accordingly an object thereof is to provide an ultrasonic testing apparatus for a pipe end portion, which enables accurate ultrasonic testing by the stable interposition of a coupling medium between the pipe end portion and an ultrasonic probe, and a method of setting the initial position of a probe holder that the ultrasonic testing apparatus has.

In order to achieve the object, the ultrasonic testing apparatus in accordance with the present invention comprises: an ultrasonic probe which is disposed under the end portion of a pipe or tube laid in the horizontal direction to face the pipe or tube end portion, the ultrasonic probe transmitting ultrasonic waves to the end portion of the pipe or tube and receiving the ultrasonic waves therefrom; and a probe holder housing the ultrasonic probe which is disposed under the end portion of the pipe or tube to face the pipe or tube end portion and follows the pipe or tube rotating in the circumferential direction. The probe holder comprises a coupling medium reserver part which surrounds a space between the ultrasonic probe and the end portion of the pipe or tube to contain a coupling medium therein. The coupling medium reserver part comprises: a coupling medium reserver part body into which the coupling medium is supplied; an annular bellows part which is attached to the upper side of the coupling medium reserver part body so as to internally communicate with the coupling medium reserver part body, and can expand and contract vertically; and an annular spacer which is attached to the upper side of the bellows part, and at least the upper surface of the annular spacer is a flat horizontal surface.

According to the ultrasonic testing apparatus in accordance with the present invention, the probe holder housing the ultrasonic probe that is disposed under the pipe or tube end portion to face the pipe or tube end portion includes the coupling medium reserver part that surrounds the space between the ultrasonic probe and the pipe or tube end portion to contain the coupling medium therein. When the coupling medium is supplied to the coupling medium reserver part body included in the coupling medium reserver part, the coupling medium flows into the annular bellows part internally communicating with the coupling medium reserver part body. The coupling medium flowing into the bellows part goes to the annular spacer attached to the bellows part and comes into contact with the pipe or tube end portion.

Since at least the upper surface of the annular spacer is a flat horizontal surface, by properly adjusting the flow rate of the coupling medium supplied to the coupling medium reserver part body, a film is formed by the coupling medium raised beyond the upper surface of the spacer by the surface tension of the coupling medium. With the film of the coupling medium in contact with the pipe or tube end portion, ultrasonic waves transmitted from the ultrasonic probe are applied to the pipe or tube end portion via the coupling medium in the coupling medium reserver part body, the coupling medium in the bellows part, and the film. The ultrasonic waves reflected by the pipe or tube end portion are received by the ultrasonic probe via the film, the coupling medium in the bellows part, and the coupling medium in the coupling medium reserver part body.

The probe holder follows the pipe or tube rotating in the circumferential direction (i.e. the probe holder is controlled to maintain the vertical and horizontal positional relationship between the probe holder and the pipe or tube). Further, the bellows part expands and contracts vertically. Therefore, even if the pipe or tube bends or has a cross section that is not a complete round, the film of the coupling medium remains in contact with the pipe or tube end portion, and the fluctuation of the film may be suppressed. Therefore, the coupling medium is interposed stably between the pipe or tube end portion and the ultrasonic probe. Thereby, accurate ultrasonic testing can be performed.

Preferably, the coupling medium reserver part further comprises a tubular member which is attached to the lower surface of the spacer and is fitted in the bellows part.

According to the above-described preferable configuration, air bubbles in the coupling medium that may be trapped in the bellows part (especially in the folded part of the bellows part) do not reach the folded part of the bellows part, and easily rise along the inner surface of the tubular member. If the coupling medium reserver part does not have the tubular member, the air bubbles trapped in the folded part of the bellows part may gather and rise as a mass at once. In this case, the ultrasonic waves are scattered by the mass of the rising air bubbles, so that the testing accuracy may be decreased. However, when the coupling medium reserver part is provided with the tubular member as in the above-described preferable configuration, the air bubbles in the coupling medium easily rise one after another along the inner surface of the tubular member before the air bubbles gather to form a mass. Therefore, the avoidance of the decrease in testing accuracy can be expected.

Preferably, the coupling medium reserver part body is provided with a coupling medium supply port for supplying the coupling medium in the tangential direction of a predetermined arc around the vertical center axis, and a coupling medium discharge port for discharging the coupling medium in the tangential direction of the arc.

According to the above-described preferable configuration, since the coupling medium is supplied in the tangential direction of a predetermined arc around the vertical center axis through the coupling medium supply port, an eddy current of the coupling medium is produced in the coupling medium reserver part body. By this eddy current, a contamination (for example, for a steel pipe or tube, droppings of scale adhering to the steel pipe or tube surface) that may be contained in the coupling medium is carried to the coupling medium discharge port and is discharged to the outside. Therefore, the coupling medium reserver part body, and in turn the whole of the coupling medium reserver part and the ultrasonic probe can be cleaned during testing, which offers an advantage of enhanced maintainability. The eddy current also offers an advantage that air bubbles that may exert an influence on the testing accuracy are less liable to adhere to the ultrasonic transmitting/receiving surface of the ultrasonic probe.

Conventionally, in the ultrasonic testing apparatus of a system in which an ultrasonic probe is immersed in a coupling medium, since air bubbles may adhere to the ultrasonic transmitting/receiving surface of the ultrasonic probe, and ultrasonic waves may be scattered by the air bubbles, testing accuracy may be reduced. Therefore, measures have been taken such that each time the testing of one pipe has been finished, the air bubbles adhering to the ultrasonic transmitting/receiving surface of the ultrasonic probe have been removed by using a jig. However, considering the online use of the ultrasonic testing apparatus, since there is a restriction as to cycle time, it is difficult to provide a step of removing air bubbles using the jig each time the testing of one pipe has been finished. Also, in the configuration such that pipe or tube testing is performed by bringing the film formed by the coupling medium raised beyond the upper surface of the spacer into contact with the pipe or tube end portion as in the ultrasonic testing apparatus in accordance with the present invention, it is necessary to set the flow rate of the coupling medium supplied to the coupling medium reserver part body relatively low so as not to fluctuate the film of coupling medium. Further, in the configuration such that the probe holder follows the pipe or tube as in the ultrasonic testing apparatus in accordance with the present invention, the flow rate of the coupling medium supplied to the coupling medium reserver part body must inevitably be made relatively low in that it is also necessary to set the volume of coupling medium reserver part body relatively low so as not to degrade the follow-up performance. Therefore, the air bubbles, once adhering to the ultrasonic transmitting/receiving surface of the ultrasonic probe, are difficult to be separated depending on the flow of the coupling medium supplied to the coupling medium reserver part body.

To solve this problem, preferably, the coupling medium reserver part body includes a coupling medium spraying nozzle for spraying the coupling medium toward the ultrasonic transmitting/receiving surface of the ultrasonic probe.

According to this preferable configuration, since the coupling medium is sprayed toward the ultrasonic transmitting/receiving surface of the ultrasonic probe through the coupling medium spraying nozzle, the air bubbles adhering to the ultrasonic transmitting/receiving surface of the ultrasonic probe are easily separated and removed, so that accurate ultrasonic testing can be performed. Also, since the adhering air bubbles can be removed efficiently only by spraying the coupling medium through the coupling medium spraying nozzle, there is offered an advantage that the ultrasonic testing apparatus in accordance with the present invention is easily used online.

To assure the stability of pipe or tube testing, an automatic ultrasonic testing apparatus is generally provided with a pre-immersing device for immersing the pipe or tube in the coupling medium in advance before testing as shown in FIG. 6. The ultrasonic testing apparatus shown in FIG. 6 has a configuration such that the ultrasonic testing apparatus includes an ultrasonic testing machine for rotating the ultrasonic probe in the circumferential direction of the pipe or tube, and pipe or tube testing is performed by moving the pipe or tube in the axial direction (the direction indicated by the dashed line in FIG. 6) without rotating the pipe or tube in the circumferential direction. In the ultrasonic testing apparatus shown in FIG. 6, since the pipe or tube is not rotated in the circumferential direction, the pre-immersing device provided at the front stage (on the upstream side in the pipe or tube movement direction) of the ultrasonic testing machine must have a configuration such that the coupling medium is sprayed toward the whole in the circumferential direction of the pipe or tube. Therefore, the ultrasonic testing apparatus becomes necessarily large in size. On the other hand, the ultrasonic testing apparatus in accordance with the present invention has a configuration such that pipe or tube testing is performed by causing the probe holder housing the ultrasonic probe to follow the pipe or tube rotating in the circumferential direction. Therefore, a mechanism part or the like for rotating the probe holder in the circumferential direction of the pipe or tube is not needed, so that the configuration other than the pre-immersing device can be made relatively small in size. However, if the large-sized pre-immersing device as shown in FIG. 6 is applied to the present invention, an advantage that the configuration other than the pre-immersing device can be made small in size (for example, an advantage that a necessary installation space can be saved) declines. Therefore, in the case where the ultrasonic testing apparatus in accordance with the present invention is provided with the pre-immersing device, in order to make the whole of the ultrasonic testing apparatus including the pre-immersing device small in size, it is preferable that the pre-immersing device for spraying the coupling medium be installed on the probe holder, and be caused to follow the pipe or tube rotating in the circumferential direction together with the probe holder.

That is to say, preferably, the ultrasonic testing apparatus in accordance with the present invention further includes the pre-immersing device installed on the probe holder and a control unit, and the control unit reciprocates the probe holder relative to the pipe or tube along the axial direction of the pipe or tube rotating in the circumferential direction, sprays the coupling medium from the pre-immersing device toward the pipe or tube when the probe holder moves forward in the pipe or tube testing range of the pipe or tube end portion, and stops the spraying of coupling medium from the pre-immersing device when the ultrasonic testing is performed while the probe holder moves backward in the pipe or tube testing range of the pipe or tube end portion.

According to this preferable configuration, since the pre-immersing device for spraying the coupling medium toward the pipe or tube is installed on the probe holder, and follows the pipe or tube rotating in the circumferential direction together with the probe holder, the whole in the circumferential direction of the pipe or tube can be pre-immersed efficiently with a small amount of coupling medium by using a small-sized pre-immersing device. Also, since the coupling medium is sprayed from the pre-immersing device toward the pipe or tube only when the probe holder moves forward in the pipe or tube testing range of the pipe or tube end portion, the coupling medium is less liable to intrude into the pipe or tube, so that stable pipe or tube testing can be performed when the probe holder moves backward in the pipe or tube testing range of the pipe or tube end portion.

Also, preferably, the control unit sprays the coupling medium from the coupling medium spraying nozzle toward the ultrasonic transmitting/receiving surface of the ultrasonic probe when the probe holder moves forward in the pipe or tube testing range of the pipe or tube end portion, and stops the spraying of coupling medium from the coupling medium spraying nozzle when the ultrasonic testing is performed while the probe holder moves backward in the pipe or tube testing range of the pipe or tube end portion.

According to this preferable configuration, when the probe holder moves forward in the pipe or tube testing range of the pipe or tube end portion, the air bubbles adhering to the ultrasonic transmitting/receiving surface of the ultrasonic probe is removed by the coupling medium sprayed from the coupling medium spraying nozzle, and on the other hand, when the ultrasonic testing is performed while the probe holder moves backward in the pipe or tube testing range of the pipe or tube end portion, the spraying of coupling medium from the coupling medium spraying nozzle is stopped. Therefore, stable testing can be performed without fluctuations of the film of coupling medium.

As the result of earnest studies conducted by the present inventors, it was found that in the ultrasonic testing apparatus in accordance with the present invention, in some cases, some of the film (the film formed by the coupling medium raised beyond the upper surface of the spacer) of the coupling medium that is in contact with the pipe or tube end portion is drawn onto the outer surface of the pipe or tube by the rotation in the circumferential direction of the pipe or tube, and entrains air bubbles during the rotation in the circumferential direction of the pipe or tube together with the pipe or tube. It was also found that, in some cases, the coupling medium involving the air bubbles rotates one turn in the circumferential direction of the pipe or tube together with the pipe or tube and intrudes again into the film of coupling medium, so that the air bubbles stay in the film of coupling medium. If the air bubbles stay in the film of coupling medium, ultrasonic waves may be scattered by the air bubbles, and the testing accuracy may be reduced.

In order to reduce possibility of air bubbles staying in the film of coupling medium as described above, it is preferable that the ultrasonic testing apparatus in accordance with the present invention further include a nozzle for spraying purge air toward a portion on the outer surface of the pipe or tube that is located on the upstream side in the direction of rotation of the pipe or tube with respect to a portion on the outer surface of the pipe or tube, which is in contact with the coupling medium staying in the coupling medium reserver part, the portion on the outer surface of the pipe or tube being located in a range not larger than 180 degrees in the circumferential direction of the pipe or tube with respect to the lowest portion of the pipe or tube.

According to this preferable configuration, the coupling medium drawn onto the outer surface of the pipe or tube, while rotating together with the pipe or tube and entraining air bubbles, is purged from the outer surface of the pipe or tube by the purge air sprayed from the nozzle, which reduces possibility of the coupling medium involving the air bubbles again intruding into the film of coupling medium raised beyond the upper surface of the spacer. Therefore, possibility of reduced testing accuracy due to the air bubbles staying in the film of coupling medium can be reduced.

As described above, in the ultrasonic testing apparatus in accordance with the present invention, the probe holder is configured so as to follow the pipe or tube rotating in the circumferential direction. That is, the probe holder is controlled so that the positional relationship with the pipe or tube in the vertical and horizontal directions is kept constant even when the pipe or tube rotates in the circumferential direction. In other words, the probe holder is controlled so that the positional relationship between the position (the initial position) of probe holder at the time of start of follow-up to the pipe or tube and the pipe or tube is kept constant (therefore, the positional relationship between the ultrasonic probe housed in the probe holder and the pipe or tube is also kept constant). Therefore, the accurate setting of the initial position of probe holder is important for performing accurate ultrasonic testing. Especially in the case where the probe holder of the ultrasonic testing apparatus in accordance with the present invention houses a first ultrasonic probe for propagating ultrasonic waves in the wall thickness direction of the pipe or tube and a pair of second ultrasonic probes disposed with the first ultrasonic probe being held therebetween to propagate ultrasonic waves in the circumferential direction of the pipe or tube, and at the assumed initial position of the probe holder, the first ultrasonic probe and the pair of second ultrasonic probes are positioned in the probe holder so that the incident points of ultrasonic waves transmitted from the first ultrasonic probe and the pair of second ultrasonic probes to the pipe or tube substantially coincide with each other, the accurate setting of the initial position of probe holder is extremely important. That is, if the actual initial position of probe holder shifts in the vertical direction from the assumed initial position, the incident points of ultrasonic waves transmitted from the pair of second ultrasonic probes to the pipe or tube, and in turn, the incident angles to the pipe or tube shift, which may reduce the accuracy of ultrasonic testing. Also, if the actual initial position of probe holder shifts in the horizontal direction from the assumed initial position, the incident points of ultrasonic waves transmitted from the first ultrasonic probe and the pair of second ultrasonic probes to the pipe or tube, and in turn, the incident angles to the pipe or tube shift, which may reduce the accuracy of ultrasonic testing.

In order to achieve the object, the present invention provides a method of setting the initial position of the probe holder that the ultrasonic testing apparatus in accordance with the present invention has, wherein the probe holder houses the first ultrasonic probe for propagating ultrasonic waves in the wall thickness direction of the pipe or tube and the pair of second ultrasonic probes disposed with the first ultrasonic probe being held therebetween to propagate ultrasonic waves in the circumferential direction of the pipe or tube as the ultrasonic probe, the first ultrasonic probe and the pair of second ultrasonic probes being positioned, at the initial position of the probe holder, in the probe holder so that the incident points of ultrasonic waves transmitted from the first ultrasonic probe and the pair of second ultrasonic probes to the pipe or tube substantially coincide with each other; and the method includes a step of adjusting the relative position in the vertical direction of the probe holder with respect to the pipe or tube so that in the state in which the probe holder does not follow the pipe or tube, a testing signal obtained by the first ultrasonic probe is displayed on an A scope, and the distance between the first ultrasonic probe and the pipe or tube that is determined by the A scope coincides with a target value, and a step of forming artificial flaws extending in the pipe or tube axial direction in a pipe end portion, and of adjusting the relative position in the horizontal direction intersecting at right angles to the pipe or tube axial direction of the probe holder with respect to the pipe or tube so that in the state in which the probe holder does not follow the pipe or tube, when the pipe or tube is rotated in the circumferential direction, the flaw signal intensities obtained by the pair of second ultrasonic probes each fall within a fixed range.

According to the method of setting the initial position of probe holder in accordance with the present invention, the testing signal obtained by the first ultrasonic probe is displayed on the A scope, and the relative position in the vertical direction of the probe holder with respect to the pipe or tube is adjusted so that the distance between the first ultrasonic probe and the pipe or tube, which is determined by the A scope, coincides with the target value, whereby the initial position in the vertical direction of the first ultrasonic probe, and in turn, the initial positions in the vertical direction of the pair of second ultrasonic probes can be set easily and accurately. Also, according to the method of setting the initial position of probe holder in accordance with the present invention, the relative position in the horizontal direction (the horizontal direction intersecting at right angles to the axial direction of the pipe or tube) of the probe holder with respect to the pipe or tube is adjusted so that when the pipe or tube is rotated in the circumferential direction, the intensities of flaw signals obtained by the pair of second ultrasonic probes fall within a fixed range (for example, within the range of about ±1 dB of the average value of flaw signal intensities), whereby the initial position in the horizontal direction of the pair of second ultrasonic probes, and in turn, the initial position in the horizontal direction of the first ultrasonic probe can be set easily and accurately.

According to the ultrasonic testing apparatus for a pipe or tube end portion in accordance with the present invention, accurate ultrasonic testing can be performed by the stable interposition of the coupling medium between the pipe or tube end portion and the ultrasonic probe. Also, according to the method of setting the initial position of probe holder in accordance with the present invention, the initial position of the probe holder, and in turn, the initial position of the ultrasonic probe can be set easily and accurately, and thereby accurate ultrasonic testing can be performed.

BEST MODE FOR CARRYING OUT THE INVENTION

One embodiment of the present invention will now be described with reference to the accompanying drawings.

Figure 1A:
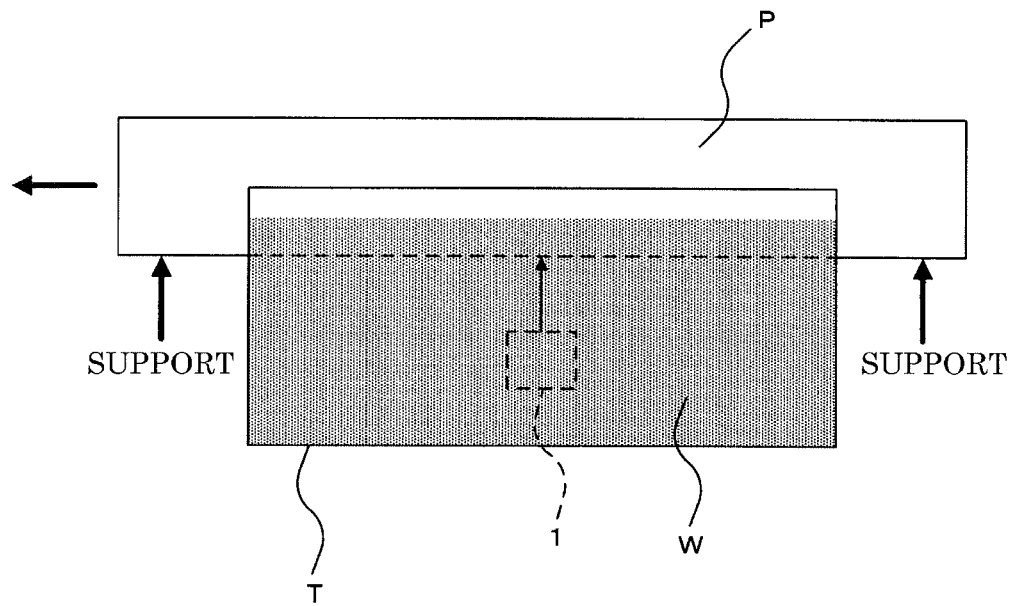
FIG. 1 (FIG. 1A and FIG. 1B) are schematic views showing a configuration of an apparatus used in ultrasonic testing of a pipe central portion, FIG. 1A being a side view, and FIG. 1B being sectional view as viewed from the front.
Figure 1B:
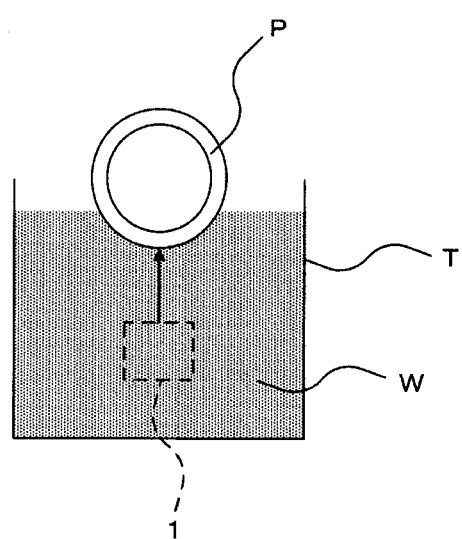
Figure 2:
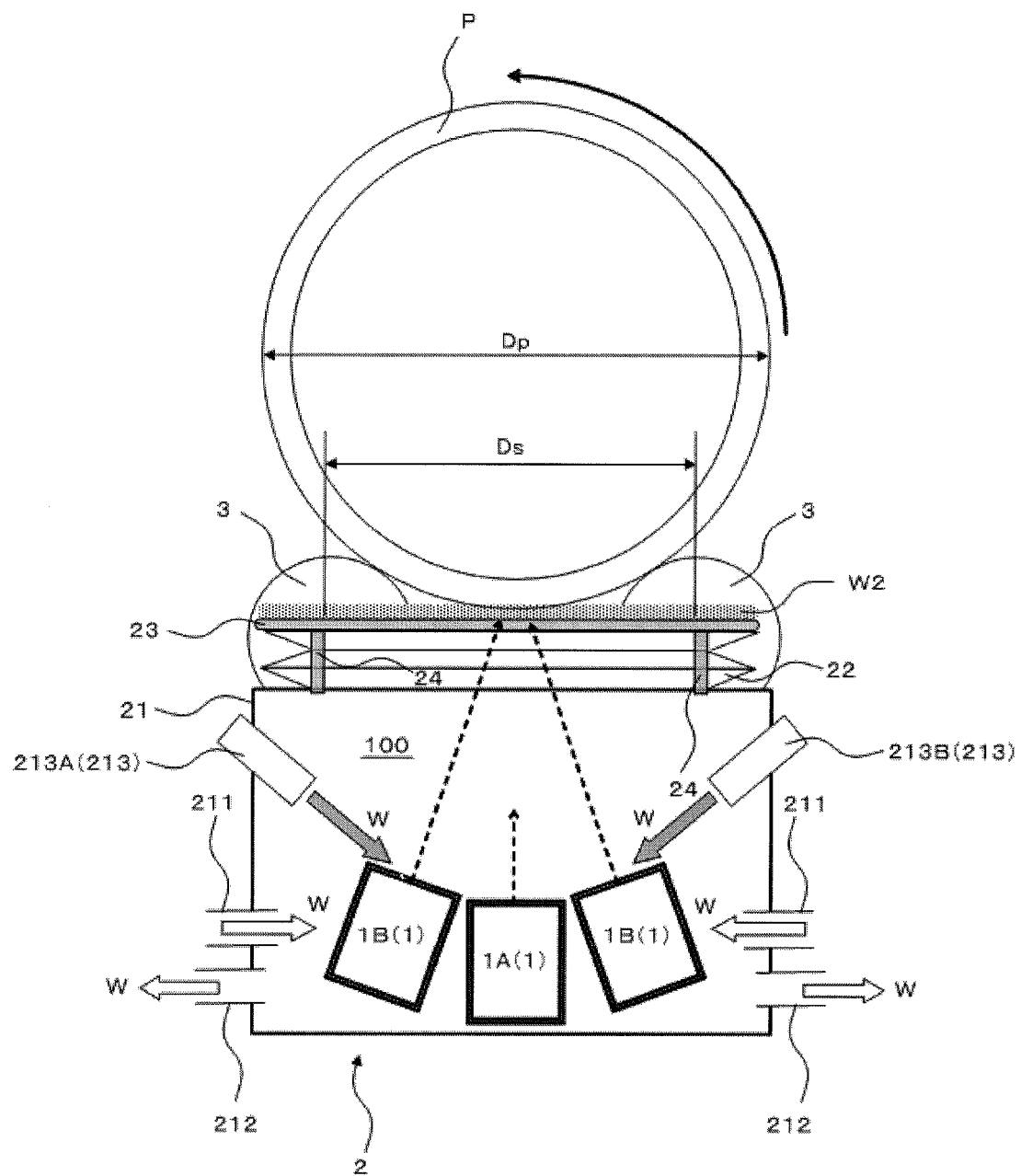
FIG. 2 is a sectional view, as viewed from the front, of an ultrasonic testing apparatus in accordance with one embodiment of the present invention.
Figure 3:
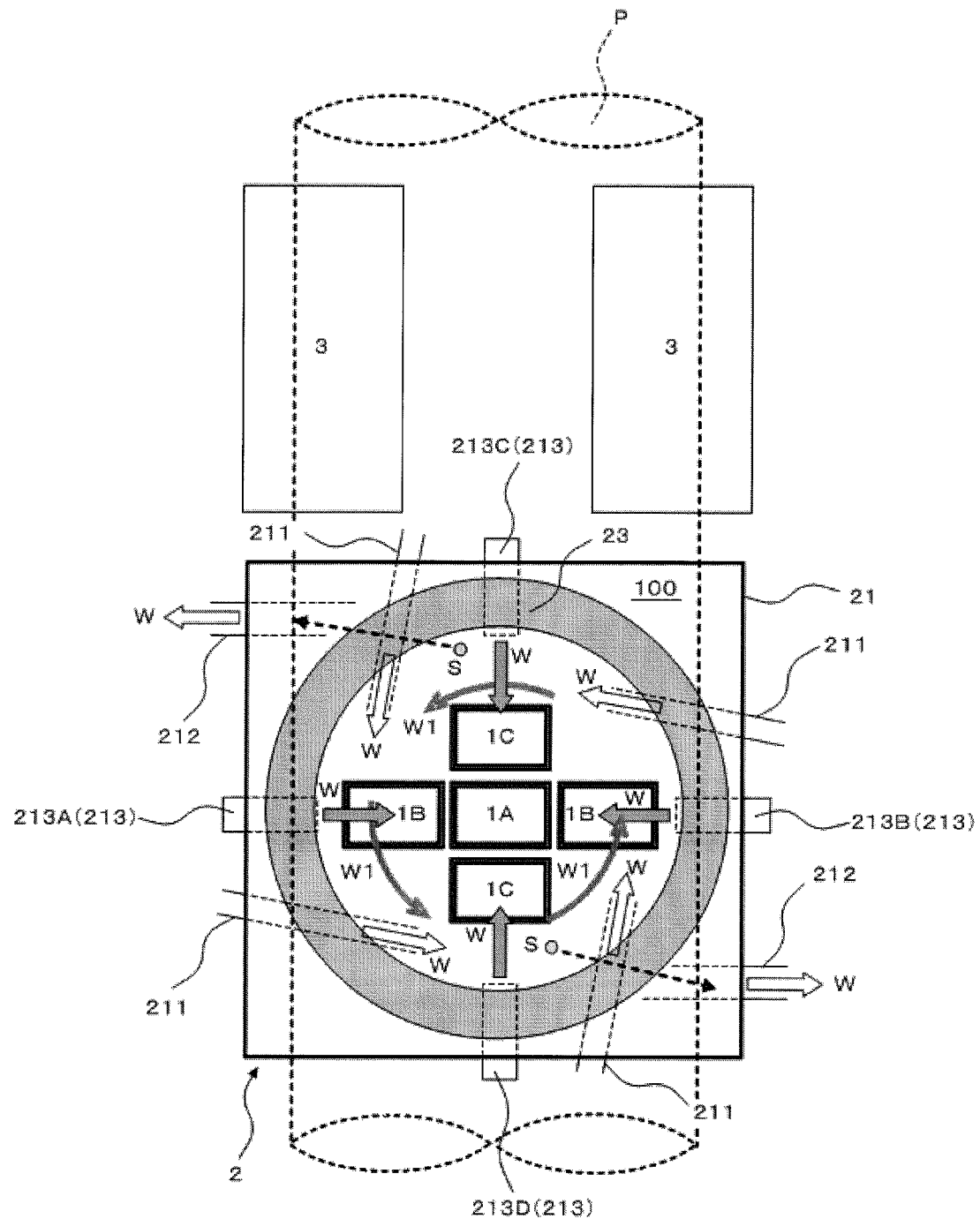
FIG. 3 is a plan view of the ultrasonic testing apparatus shown in FIG. 2.

FIG. 2 is a sectional view, as viewed from the front, of an ultrasonic testing apparatus in accordance with one embodiment of the present invention. FIG. 3 is a plan view of the ultrasonic testing apparatus shown in FIG. 2.

As shown in FIG. 2 or FIG. 3, the ultrasonic testing apparatus 100 of this embodiment comprises an ultrasonic probe 1 which is disposed under the end portion of a pipe P laid in the horizontal direction to face the pipe P end portion, the ultrasonic probe 1 transmitting ultrasonic waves to the end portion of the pipe P and receiving the ultrasonic waves therefrom; and a probe holder 2 housing the ultrasonic probe 1 which is disposed under the end portion of the pipe P to face the pipe P end portion and follows the pipe P rotating in the circumferential direction.

The pipe P is placed on turning rollers 3, so that the pipe P is rotated in the circumferential direction thereof by the rotation of the turning rollers 3. The probe holder 2 is disposed under the end portion of the pipe P projecting from the turning rollers 3 to face the pipe end portion.

The ultrasonic testing apparatus 100 of this embodiment is provided with an ultrasonic probe 1A, ultrasonic probes 1B (two probes), and ultrasonic probes 1C (two probes), all of which constitute the ultrasonic probe 1. The ultrasonic probe 1A is used to detect lamination (a planar flaw parallel to the inner and outer surfaces of the pipe P) by propagating ultrasonic waves in the wall thickness direction of the pipe P. The ultrasonic probes 1B are inclined in the circumferential direction of the pipe P, and are used to detect an axial flaw (a flaw extending in the axial direction of the pipe P) by propagating ultrasonic waves in the circumferential direction of the pipe P. The ultrasonic probes 1C are inclined in the axial direction of the pipe P, and are used to detect a circumferential flaw (a flaw extending in the circumferential direction of the pipe P) by propagating ultrasonic waves in the axial direction of the pipe P. At a position at which the probe holder 2 follows the pipe P, these ultrasonic probes 1A to 1C are positioned in the probe holder so that the incident points of the transmitted ultrasonic waves to the pipe P coincide substantially with each other.

The probe holder 2 of this embodiment is, as described above, configured to follow the pipe P rotating in the circumferential direction. Specifically, the probe holder 2 is attached to a follow-up device (not shown). This follow-up device moves the probe holder 2 vertically and horizontally to maintain the vertical and horizontal positional relationship between the probe holder 2 and the pipe P (thereby, also maintaining the positional relationship between the ultrasonic probe 1 housed in the probe holder 2 and the pipe P) on the basis of a measurement result of displacement of the outer surface of the rotating pipe P. In other words, the follow-up device controls the position of the probe holder 2 so that the positional relationship between the position (initial position) of the probe holder 2 at the time when the follow-up to the pipe P is started and the pipe P is kept constant (therefore, so that the positional relationship between the ultrasonic probes 1A to 1C housed in the probe holder 2 and the pipe P is kept constant). Although the above-described follow-up device is not subject to any special restriction and various publicly known follow-up devices can be employed, the follow-up device described in, for example, JP2008-139191A is preferably employed.

The probe holder 2 includes a coupling medium reserver part that surrounds a space between the ultrasonic probe 1 and the end portion of the pipe P to contain a coupling medium W such as water therein. In this embodiment, since the whole of the probe holder 2 functions as the coupling medium reserver part, in the explanation below, the same reference numeral as that of the probe holder 2 is applied to the coupling medium reserver part.

The coupling medium reserver part 2 includes a coupling medium reserver part body 21, an annular (in this embodiment, ring-shaped) bellows part 22, and an annular (in this embodiment, ring-shaped) spacer 23. Also, the coupling medium reserver part 2 of this embodiment includes a tubular (in this embodiment, cylindrical) member 24 as a preferable configuration.

The coupling medium reserver part body 21 of this embodiment includes coupling medium supply ports 211 (in this embodiment, four ports) and coupling medium discharge ports 212 (in this embodiment, two ports). Into and from the coupling medium reserver part body 21, the coupling medium W is supplied through the coupling medium supply ports 211, and the coupling medium W is discharged through the coupling medium discharge ports 212. The flow rate of the coupling medium W supplied through the coupling medium supply ports 211 (the total flow rate supplied through the four coupling medium supply ports 211) is set higher than the flow rate of the coupling medium W discharged through the coupling medium discharge ports 212 (the total flow rate discharged through the two coupling medium discharge ports 212). For example, the flow rate of the coupling medium W discharged through the coupling medium discharge ports 212 is set at about 10 to 15% of the flow rate of the coupling medium W supplied through the coupling medium supply ports 211. Therefore, the coupling medium W stays in the coupling medium reserver part body 21.

In this embodiment, as a preferable configuration, the coupling medium supply ports 211 are arranged so that the coupling medium W is supplied in the tangential direction of a predetermined arc around the vertical center axis. Specifically, the coupling medium supply ports 211 extend in the tangential direction of the aforementioned arc. Also, the coupling medium discharge ports 212 are arranged so that the coupling medium W is discharged in the tangential direction of the aforementioned arc. Specifically, the coupling medium discharge ports 212 extend in the tangential direction of the aforementioned arc. Since the coupling medium W is supplied in the tangential direction of the aforementioned arc through the coupling medium supply ports 211, an eddy current W1 of the coupling medium W is produced in the coupling medium reserver part body 21. By this eddy current W1, a contamination (for example, for a steel pipe P, droppings of scale S adhering to the steel pipe surface) that may be contained in the coupling medium W is carried to the coupling medium discharge ports 212 and is discharged to the outside. Therefore, the coupling medium reserver part body 21, and in turn the whole of the coupling medium reserver part 2 and the ultrasonic probe 1 can be cleaned during testing, which offers an advantage of enhanced maintainability. The eddy current W1 also offers an advantage that air bubbles that may exert an influence on the testing accuracy are less liable to adhere to the ultrasonic transmitting/receiving surface of the ultrasonic probe 1.

The flow rate of the coupling medium W supplied through the coupling medium supply ports 211 is preferably adjusted to about 2 to 6 liters/minute. At this time, the flow rate of the coupling medium W discharged through the coupling medium discharge ports 212 is about 10 to 15% of the supply flow rate, being lower than 1 liter/minute. If the flow rate of the coupling medium W is lower than 2 liters/minute, the shortage of flow rate makes it difficult to form a film W2 that is formed by the coupling medium W rising beyond the upper surface of the spacer 23. Also, if the flow rate of the coupling medium W is higher than 6 liters/minute, the excess flow rate raises the possibility that the film W2 of the coupling medium rising beyond the upper surface of the spacer 23 may fall into disorder. The flow rate of the coupling medium W supplied through the coupling medium supply ports 211 is set in the above-described range, and as described later, an inside diameter Ds of the spacer 23 is set at 25% or more of an outside diameter Dp of the pipe P, whereby the thickness of the film W2 of the coupling medium can be controlled to about 2 to 3 mm.

Also, the coupling medium reserver part body 21 of this embodiment includes, as a preferable configuration, a coupling medium spraying nozzle 213 for spraying the coupling medium W such as water toward the ultrasonic transmitting/receiving surfaces of the ultrasonic probes 1A to 1C. In this embodiment, as the coupling medium spraying nozzle 213, a coupling medium spraying nozzle 213A for spraying the coupling medium W toward the ultrasonic transmitting/receiving surface of one ultrasonic probe 1B, a coupling medium spraying nozzle 213B for spraying the coupling medium W toward the ultrasonic transmitting/receiving surface of the other ultrasonic probe 1B, a coupling medium spraying nozzle 213C for spraying the coupling medium W toward the ultrasonic transmitting/receiving surface of one ultrasonic probe 1C, and a coupling medium spraying nozzle 213D for spraying the coupling medium W toward the ultrasonic transmitting/receiving surface of the other ultrasonic probe 1C. The coupling medium spraying nozzles 213A to 213D also perform the function of spraying the coupling medium W toward the ultrasonic transmitting/receiving surface of the ultrasonic probe 1A.

Since the coupling medium W is sprayed toward the ultrasonic transmitting/receiving surfaces of the ultrasonic probes 1A to 1D through the coupling medium spraying nozzle 213 of this embodiment, the air bubbles adhering to the ultrasonic transmitting/receiving surfaces of the ultrasonic probes 1A to 1D can be separated and removed easily, which enables accurate ultrasonic testing. Also, merely by spraying the coupling medium W through the coupling medium spraying nozzle 213, the adhering air bubbles can be removed efficiently, which offers an advantage that the ultrasonic testing apparatus 100 in accordance with this embodiment can easily be used online.

The flow rate of the coupling medium W sprayed through the coupling medium spraying nozzle 213 is preferably adjusted so as to be higher than the flow rate of the coupling medium W supplied through the coupling medium supply ports 211. Concretely, the flow rate of the coupling medium W sprayed through the coupling medium spraying nozzle 213 is preferably adjusted to about 16 to 18 liters/minute. If the flow rate of the coupling medium W sprayed through the coupling medium spraying nozzle 213 is set at 16 liters/minute or higher, the air bubbles adhering to the ultrasonic transmitting/receiving surface of the ultrasonic probes 1A to 1D can be separated and removed efficiently and easily. On the other hand, if the flow rate of the coupling medium W sprayed through the coupling medium spraying nozzle 213 is set excessively high, the ultrasonic transmitting/receiving surface of the ultrasonic probes 1A to 1D may be damaged. Therefore, the flow rate of the coupling medium W sprayed through the coupling medium spraying nozzle 213 is set at 18 liters/minute or lower.

The bellows part 22 of this embodiment is attached to the upper side of the coupling medium reserver part body 21 so as to internally communicate with the coupling medium reserver part body 21, and can expand and contract vertically. Specifically, an opening (in this embodiment, a circular opening) is formed in the upper surface of the coupling medium reserver part body 21, and the annular bellows part 22 is installed so as to surround this opening. The innermost diameter of the bellows part 22 is set approximately equal to (equal to or slightly smaller than) the diameter of the opening.

The material for forming the bellows part 22 is not subject to any special restriction. However, a material having high wear resistance and expandability is preferably used. High wear resistance is useful for suppressing a breakage in the folded part of the bellows part 22 caused by repeated expansion and contraction of the bellows part 22. High expandability is useful for suppressing the fluctuation of the film W2 due to the direct transmission of an impact caused by the contact of the pipe P with the spacer 23 to the film W2 of the coupling medium. As a material for forming the bellows part 22, silicone rubber is preferably used because of its high wear resistance and expandability.

The spacer 23 of this embodiment is attached to the upper side of the bellows part 22, and at least the upper surface of the spacer (in this embodiment, the lower surface thereof, too) is a flat horizontal surface. Also, the tubular member 24 of this embodiment is attached to the lower surface of the spacer 23, and is fitted in the bellows part 22. Specifically, the outside diameter of the tubular member 24 is set approximately equal to (equal to or slightly smaller than) the innermost diameter of the bellows part 22 so that the tubular member 24 is fitted in the bellows part 22. Thereby, the outside diameter of the tubular member 24 is set approximately equal to (equal to or slightly smaller than) the diameter of the opening formed in the upper surface of the coupling medium reserver part body 21. Therefore, when the spacer 23 attached to the bellows part 22 is lowered by the contraction of the bellows part 22 and accordingly the tubular member 24 is also lowered, the lower end portion of the tubular member 24 passes through the opening in the coupling medium reserver part body 21 and is inserted into the coupling medium reserver part body 21. The spacer 23 is preferably formed of a stainless steel having high wear resistance because the frequency of contact of the spacer 23 with the end portion of the steel pipe P is high. Further preferably, the spacer 23 and the tubular member 24 are formed integrally of a stainless steel.

As a method for attaching the spacer 23 to the bellows part 22, a method may be employed in which the spacer 23 is directly fixed to the upper portion of the bellows part 22 using machine screws or the like. However, the spacer 23 of this embodiment is mounted with the tubular member 24, and the tubular member 24 is fitted in the bellows part 22. Therefore, even if the spacer 23 is not fixed directly to the bellows part 22, the spacer 23 is attached to the bellows part 22 via the tubular member 24 in a state of being relatively stable.

Figure 4:
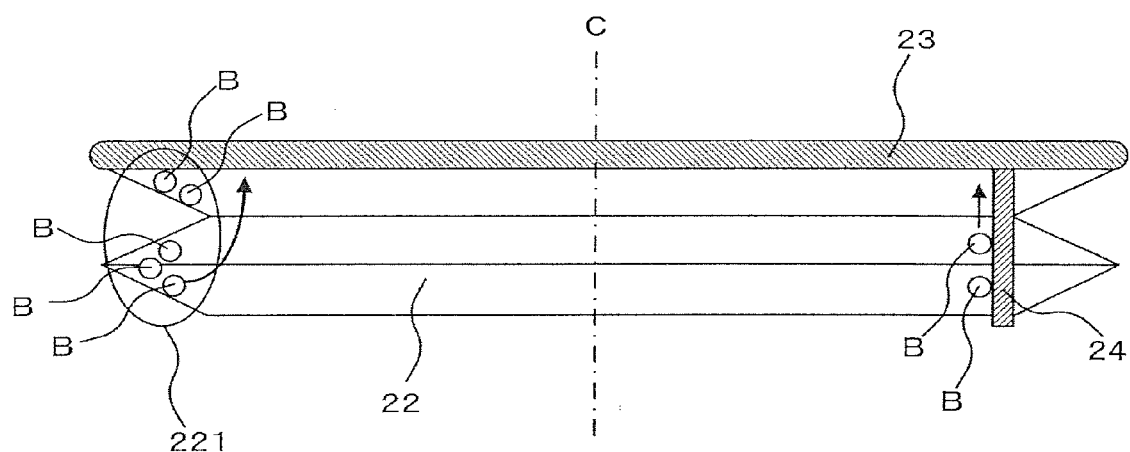
FIG. 4 is a sectional view, as viewed from the front, for explaining the operation of a tubular member shown in FIG. 2.

FIG. 4 is a sectional view, as viewed from the front, for explaining the operation of the tubular member 24 of this embodiment. In FIG. 4, the left-hand side of a dashed line C shows a state in which the tubular member 24 is not provided, and the right-hand side thereof shows a state in which the tubular member 24 is provided. As shown in FIG. 4, since the coupling medium reserver part 2 of this embodiment is provided with the tubular member 24, air bubbles B in the coupling medium W do not reach a folded part 221 of the bellows part 22, and easily rise along the inner surface of the tubular member 24. If the coupling medium reserver part 2 does not have the tubular member 24, the air bubbles B trapped in the folded part 221 of the bellows part 22 may gather and rise as a mass at once. In this case, the ultrasonic waves are scattered by the mass of the rising air bubbles B, so that the testing accuracy may be decreased. In contrast, when the coupling medium reserver part 2 is provided with the tubular member 24, the air bubbles B in the coupling medium W easily rise one after another along the inner surface of the tubular member 24 before the air bubbles B gather to form a mass. Therefore, the avoidance of the decrease in testing accuracy can be expected.

The inside diameter Ds of the spacer 23 shown in FIG. 2 is preferably set at 25% or more of the outside diameter Dp of the pipe P. If the inside diameter Ds of the spacer 23 is too small as compared with the outside diameter Dp of the pipe P (less than 25%), the opening of the spacer 23 is easily closed by the outer surface of the pipe P (a state close to the state in which the outer surface of the pipe P is in surface contact with the opening of the spacer 23 is formed), and therefore the possibility that the film of the coupling medium W2 may fall into disorder rises. If the inside diameter Ds of the spacer 23 is too large, the size of the probe holder (coupling medium reserver part) 2 increases accordingly, so that the weight of the whole of the probe holder 2 including the weight of the coupling medium W staying in the probe holder 2 increases, whereby the follow-up performance of the probe holder 2 may be deteriorated. Therefore, attention must be paid to the fact that the inside diameter Ds of the spacer 23 should not be set excessively large.

In the ultrasonic testing apparatus 100 of this embodiment, which has been explained above, when the coupling medium W is supplied to the coupling medium reserver part body 21, the coupling medium W flows into the bellows part 22 internally communicating with the coupling medium reserver part body 21. The coupling medium W flowing into the bellows part 22 goes to the spacer 23 attached to the bellows part 22 and comes into contact with the end portion of the pipe P.

Since at least the upper surface of the spacer 23 is a flat horizontal surface, by adjusting the flow rate of the coupling medium W supplied to the coupling medium reserver part body 21 to a proper range as described above, the film W2 is formed by the coupling medium W raised beyond the upper surface of the spacer 23 by the surface tension of the coupling medium W. With the film W2 of the coupling medium in contact with the end portion of the pipe P, ultrasonic waves transmitted from the ultrasonic probe 1 are applied to the end portion of the pipe P via the coupling medium W in the coupling medium reserver part body 21, the coupling medium W in the bellows part 22, and the film W2. The ultrasonic waves reflected by the end portion of the pipe P are received by the ultrasonic probe 1 via the film W2, the coupling medium W in the bellows part 22, and the coupling medium W in the coupling medium reserver part body 21.

The probe holder 2 follows the pipe P rotating in the circumferential direction. Further, the bellows part 22 expands and contracts vertically. Therefore, even if the pipe P bends or has a cross section that is not a complete round, the film W2 of the coupling medium remains in contact with the end portion of the pipe P, and the fluctuation of the film may be suppressed. Therefore, the coupling medium W (including the film W2) is interposed stably between the end portion of the pipe P and the ultrasonic probe 1. Thereby, accurate ultrasonic testing can be performed.

Figure 5A:
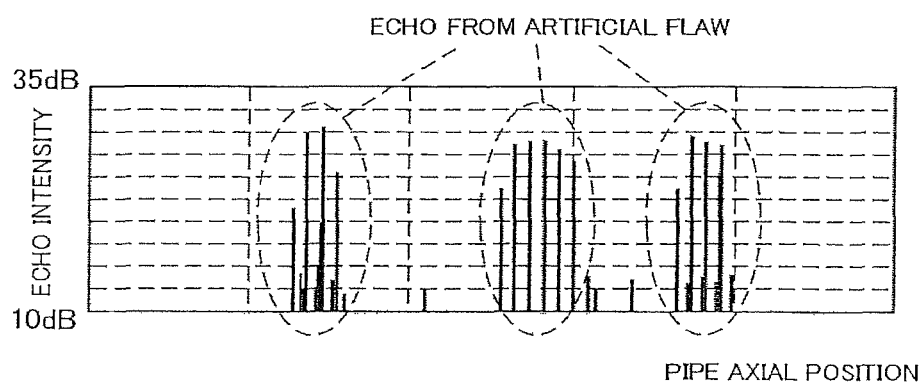
FIG. 5 (FIG. 5A and FIG. 5B) are views showing one example of detection results of artificial flaws formed in a pipe end portion, FIG. 5A being a flaw detection chart obtained by an ultrasonic probe for detecting axial flaws, and FIG. 5B being a schematic view showing the artificial flaws.
Figure 5B:
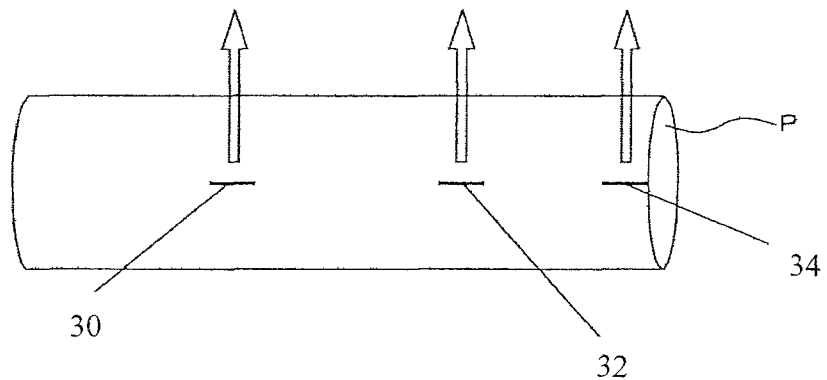
Figure 6:
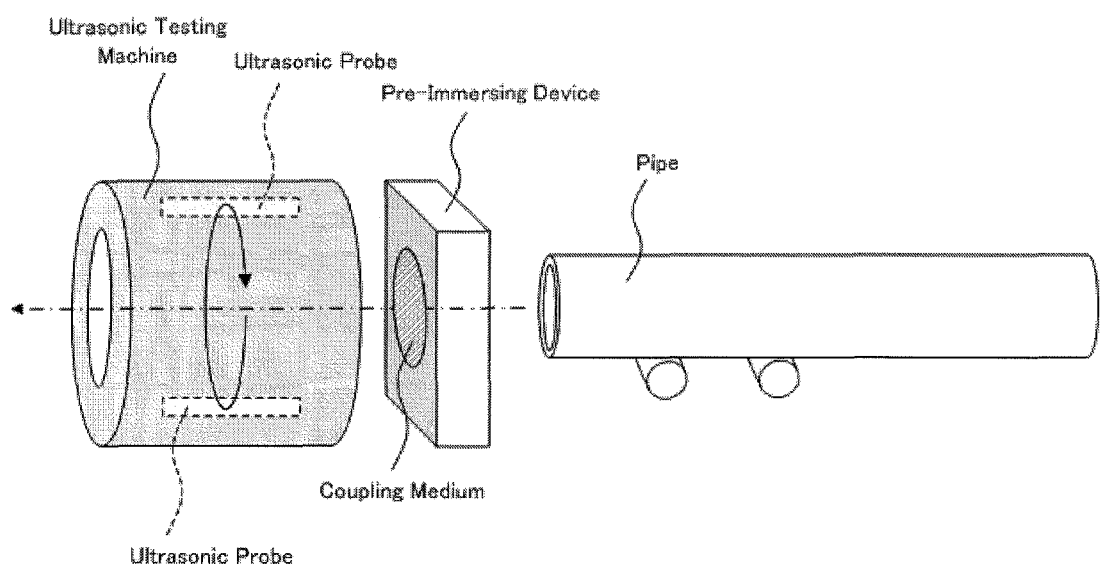
FIG. 6 is a perspective view schematically showing a general configuration of a conventional ultrasonic testing apparatus including a pre-immersing device.

FIGS. 5A and 5B are views showing one example of results of detection of artificial flaws (axial flaws) formed on the outer surface in the end portion of pipe P, which is made under the following conditions (1) to (6) by using the ultrasonic testing apparatus 100 of this embodiment. FIG. 5A is a flaw detection chart obtained by the ultrasonic probes 1B for detecting axial flaws, and FIG. 5B is a schematic view showing the artificial flaws. The flaws in FIG. 5B are identified as 30, which represents an artificial flaw for confirming flaw detectability at a testing start position. 32 represents a second artificial flaw for calibrating flaw detection sensitivity of ultrasonic probe 1B. 34 represents a third artificial flaw confirming flaw detectability at the pipe end. The abscissas of FIG. 5A represent the axial position of the pipe P, and the ordinates thereof represent echo intensity.

(1) Outside diameter of pipe P: 168 mm
(2) Rotational speed of pipe P: 113 rpm
(3) Travel speed in pipe axial direction of probe holder 2: 15.1 mm/sec
(4) Inside diameter Ds of spacer 23: 63 mm
(5) Flow rate of coupling medium (water) supplied: 5.5 liters/min
(6) Flow rate of coupling medium (water) discharged: less than 1 liter/min As can be seen from FIG. 5A, according to the ultrasonic testing apparatus 100 of this embodiment, the coupling medium can be interposed stably between the pipe end portion and the ultrasonic probe, and the artificial flaws can be detected with high accuracy. FIG. 5 shows the detection results of axial flaws only. However, it was able to confirm that in the case where circumferential flaws are formed as artificial flaws and testing is performed, the flaws can be detected with high accuracy by using the ultrasonic probes 1C, and in the case where a flat-bottomed holes are formed as artificial flaws and testing is performed, the flaws can be detected with high accuracy by using the ultrasonic probe 1A.

First Modification

The ultrasonic testing apparatus 100 in accordance with this embodiment is preferably provided with a pre-immersing device to assure the stability of pipe testing.

Figure 7A:
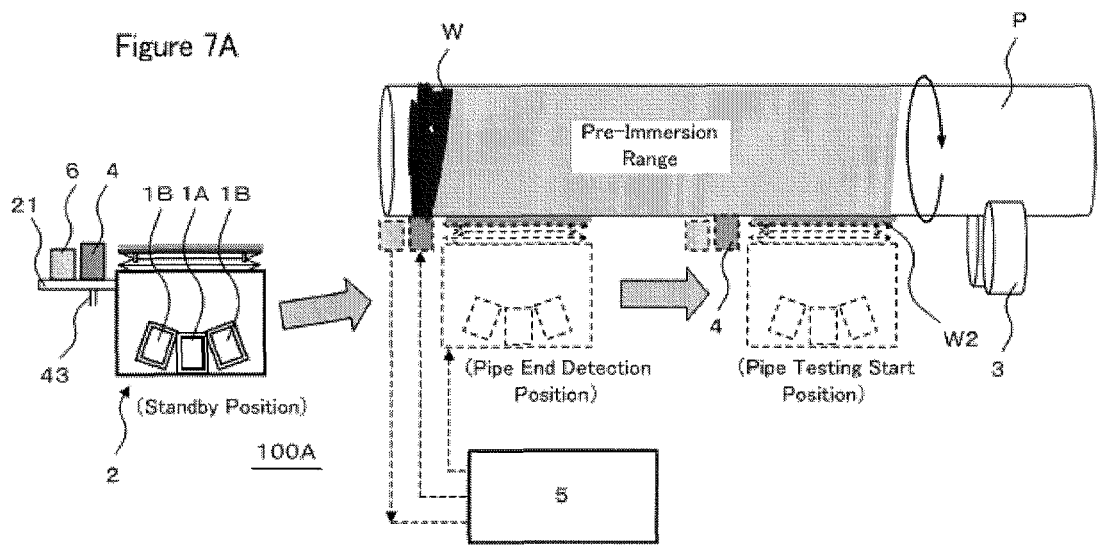
FIG. 7 (FIG. 7A, FIG. 7B, and FIG. 7C) are schematic views showing a general configuration and operation of an ultrasonic testing apparatus in accordance with a first modification of the present invention, which includes a pre-immersing device, FIG. 7A being a schematic view for explaining the operation at the time of pre-immersion, FIG. 7B being a schematic view for explaining the operation at the time of pipe testing, and FIG. 7C being a sectional view of the pre-immersing device.
Figure 7B:
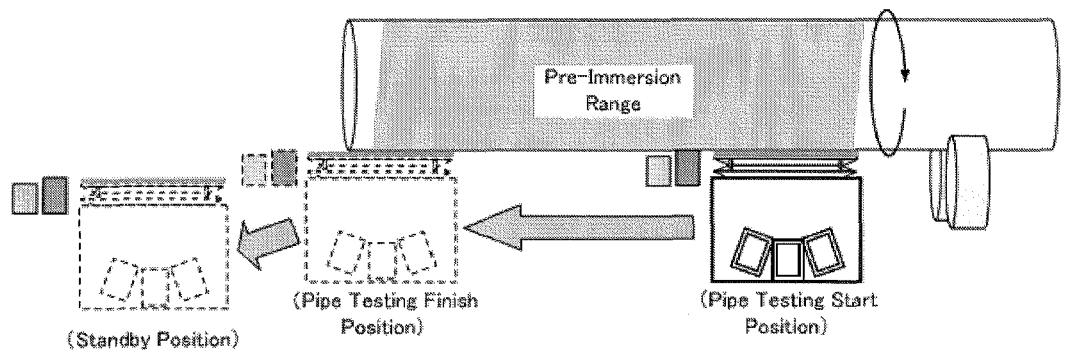
Figure 7C:
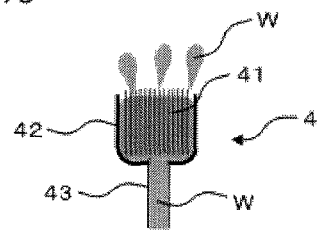

FIG. 7A, FIG. 7B, and FIG. 7C are schematic views showing a general configuration and operation of an ultrasonic testing apparatus in accordance with a first modification of this embodiment, which includes the pre-immersing device. FIG. 7A is a schematic view for explaining the operation at the time of pre-immersion, FIG. 7B is a schematic view for explaining the operation at the time of pipe testing, and FIG. 7C is a sectional view of the pre-immersing device.

As shown in FIG. 7A, FIG. 7B, and FIG. 7C, an ultrasonic testing apparatus 100A in accordance with the first modification includes a pre-immersing device 4 and a control unit 5 in addition to the configuration of the above-described ultrasonic testing apparatus 100. Also, as a preferable configuration, the ultrasonic testing apparatus 100A includes a pipe end detecting sensor 6.

The pre-immersing device 4 and the pipe end detecting sensor 6 of this modification are installed on a base 21 (refer to the probe holder 2 at the standby position shown in FIG. 7A. The illustration of the base 21 is omitted for other probe holders 2 in FIG. 7A and FIG. 7B) provided on the probe holder 2. The pipe end detecting sensor 6 is installed at a position on the upstream side in the forward movement direction of the probe holder 2 shown in FIG. 7A with respect to the pre-immersing device 4. The pre-immersing device 4 and the pipe end detecting sensor 6 follow the pipe P together with the probe holder 2.

As shown in FIG. 7C, the pre-immersing device 4 of this modification includes a metallic brush 41, a rubber-made covering member 42 that covers the periphery of the brush 41, and a hose 43 for supplying the coupling medium W into the covering member 42, and in turn, into the gaps between the wire rods constituting the brush 41. The upper end of the covering member 42 is open, and the lower end thereof communicates with the hose 43.

As the pipe end detecting sensor 6 of this modification, a reflective-type photoelectric sensor provided with a projector and a photoreceiver is used. That is, the pipe end detecting sensor 6 is configured so that a pipe end is detected by utilizing a phenomenon that the quantity of light received by the photoreceiver increases in the case where light emitted from the projector is applied to the pipe P and is reflected by the pipe P as compared with the case where light is not applied to the pipe P.

The control unit 5 of this modification performs the function of driving a stage (not shown) for reciprocating the probe holder 2 and a follow-up device (not shown) as a unit along the vertical direction and the axial direction of the pipe P and the function of driving the pre-immersing device 4 according to the detection of the pipe end of the pipe P using the pipe end detecting sensor 6 (specifically, turning on and off the supply of the coupling medium W to the hose 43 by controlling an electromagnetic valve or the like interposed between the supply source of the coupling medium W and the hose 43). The control unit 5 of this modification also performs the function of driving the above-described coupling medium spraying nozzle 213 (specifically, turning on and off the supply of the coupling medium W to the coupling medium spraying nozzle 213 by controlling an electromagnetic valve or the like interposed between the supply source of the coupling medium W and the coupling medium spraying nozzle 213).

Hereunder, the operation of the ultrasonic testing apparatus 100A having the above-described configuration is explained.

At the time of pre-immersion shown in FIG. 7A, the control unit 5 drives the stage to gradually raise the probe holder 2 at the standby position located away from the pipe end side of the pipe P, and at the same time, to move the probe holder 2 forward along the axial direction of the pipe P rotating in the circumferential direction (in the example shown in FIGS. 7A and 7B, to move the probe holder 2 from the pipe end side of the pipe P toward the pipe center side). The control unit 5 begins to supply the coupling medium W to the coupling medium spraying nozzle 213 at the timing of beginning the drive of the stage. Thereby, the coupling medium W is sprayed from the coupling medium spraying nozzle 213 toward the ultrasonic transmitting/receiving surface of the ultrasonic probe 1, whereby the air bubbles adhering to the ultrasonic transmitting/receiving surface of the ultrasonic probe 1 are separated and removed. The control unit 5 stops the raising operation of the probe holder 2 at a preset height at which the tip end (upper end) of the brush 41 of the pre-immersing device 4 can be in contact with the outer surface of the pipe P, and subsequently, moves the probe holder 2 forward along the axial direction of the pipe P. At this time, the control unit 5 begins to supply the coupling medium W to the hose 43 of the pre-immersing device 4 at the timing of detection of the pipe end of the pipe P using the pipe end detecting sensor 6. Thereby, the coupling medium W is sprayed toward the pipe P from the gaps between the wire rods constituting the brush 41 of the pre-immersing device 4. In the state in which the coupling medium W is sprayed from the pre-immersing device 4 toward the pipe P in this manner, the probe holder 2 moves forward to the preset pipe testing start position along the axial direction of the pipe P while following the pipe P by means of the follow-up device. Of the pipe testing range of the end portion of the pipe P, in the range through which the pre-immersing device 4 passes, pre-immersion is performed by the coupling medium W sprayed from the pre-immersing device 4. In a range other than the above-described range, pre-immersion is performed by a film W2 of the coupling medium.

At the time of pipe testing shown in FIG. 7B, the control unit 5 drives the stage to move the probe holder 2 at the pipe testing start position backward (in the example shown in FIGS. 7A and 7B, to move the probe holder 2 from the pipe center side of the pipe P toward the pipe end side). At this time, the control unit 5 stops the supply of the coupling medium W to the hose 43 of the pre-immersing device 4. Also, at this time, the control unit 5 stops the supply of the coupling medium W to the coupling medium spraying nozzle 213. The probe holder 2 moves backward along the axial direction of the pipe P from the pipe testing start position to a preset pipe testing finish position while following the pipe P by means of the follow-up device, and during this time, ultrasonic testing is performed. After the finish of ultrasonic testing, the control unit 5 further moves the probe holder 2 backward along the axial direction of the pipe P, and at the same time, gradually lowers the probe holder 2 to the standby position.

According to the ultrasonic testing apparatus 100A described above, since the pre-immersing device 4 for spraying the coupling medium W toward the pipe P is installed on the probe holder 2, and follows the pipe P rotating in the circumferential direction together with the probe holder 2, the whole in the circumferential direction of the pipe P can be pre-immersed efficiently with a small amount of coupling medium W by using a small-sized pre-immersing device 4. Also, since the coupling medium W is sprayed from the pre-immersing device 4 toward the pipe P only when the probe holder 2 moves forward in the pipe testing range of the pipe end portion (moreover, in this modification, the coupling medium W is sprayed after the timing at which the pipe end detecting sensor 6 installed at a position on the upstream side in the forward movement direction of the probe holder 2 with respect to the pre-immersing device 4 detects the pipe end of the pipe P), the coupling medium W is less liable to intrude into the pipe P, so that stable pipe testing can be performed when the probe holder 2 moves backward in the pipe testing range of the pipe end portion. Also, in this modification, the configuration is such that the pre-immersing device 4 is provided with the brush 41, and pre-immersion is performed while the brush 41 is in contact with the outer surface of the pipe P (while the brush 41 slides on the outer surface of the pipe P along the circumferential direction and the axial direction of the pipe P). That is, since the configuration is such that the coupling medium W is applied onto the outer surface of the pipe P by using the brush 41, the pipe P can be pre-immersed more efficiently, and also contamination on the outer surface of the pipe P that may exert an influence on the testing accuracy can be removed efficiently. Further, in this modification, when the probe holder 2 moves forward in the pipe testing range of the pipe end portion, the air bubbles adhering to the ultrasonic transmitting/receiving surface of the ultrasonic probe 1 are removed by the coupling medium W sprayed from the coupling medium spraying nozzle 213, and on the other hand, when the ultrasonic testing is performed while the probe holder 2 moves backward in the pipe testing range of the pipe end portion, the spraying of coupling medium from the coupling medium spraying nozzle 213 is stopped, so that stable testing can be performed without fluctuations of the film W2 of coupling medium.

In this modification, as the preferable configuration for detecting the pipe end surely, the configuration in which the pipe end detecting sensor 6 is provided has been explained. However, the pipe end detecting sensor 6 is not necessarily needed to perform the pre-immersion of the pipe P. That is, in the case where the pipe end position of the pipe P (the position along the axial direction of the pipe P) can be assumed to be almost fixed for any pipe P, a position corresponding to the pipe end detection position shown in FIG. 7A has only to be set beforehand in the control unit 5. In this case, the supply of the coupling medium W to the hose 43 of the pre-immersing device 4 has only to be started at the timing of arrival of the probe holder 2 at this preset position.

Also, in this modification, explanation has been given of the configuration such that pre-immersion is performed when the probe holder 2 is moved from the pipe end side of the pipe P toward the pipe center side, and testing is performed when the probe holder 2 is moved from the pipe center side of the pipe P toward the pipe end side. Inversely, however, the configuration can be made such that pre-immersion is performed when the probe holder 2 is moved from the pipe center side of the pipe P toward the pipe end side, and testing is performed when the probe holder 2 is moved from the pipe end side of the pipe P toward the pipe center side. The same is also true for the spraying of the coupling medium W from the coupling medium spraying nozzle 213.

Second Modification

The ultrasonic testing apparatus 100 in accordance with this embodiment is preferably provided with a nozzle for spraying purge air onto the outer surface of the pipe P to reduce possibility of air bubbles staying in the film W2 of the coupling medium.

Figure 8A:
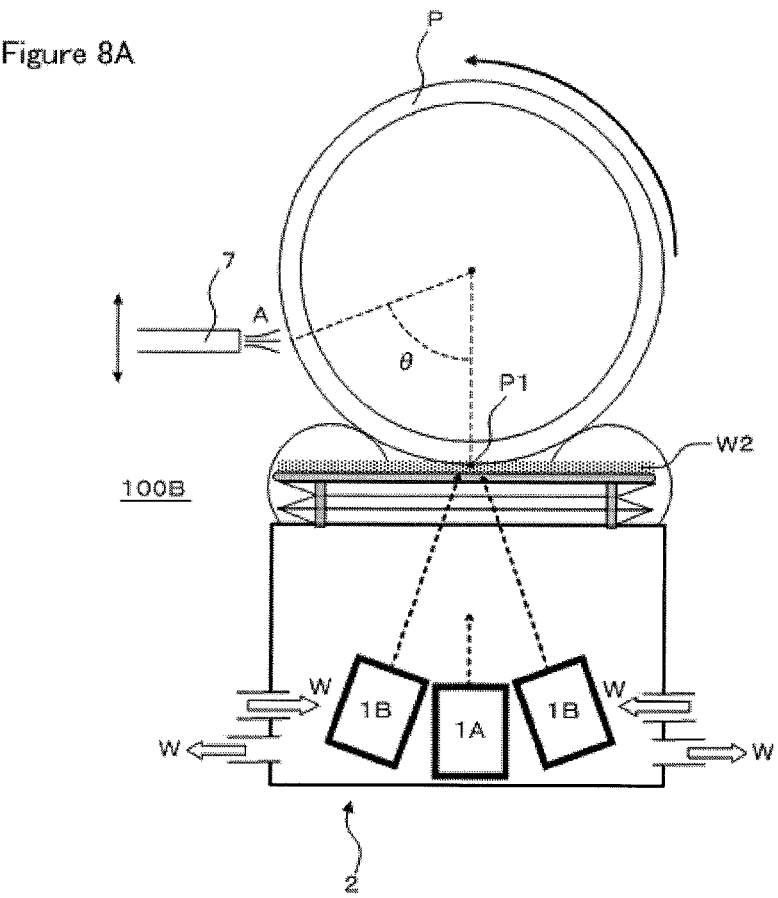
FIG. 8 (FIG. 8A, FIG. 8B, and FIG. 8C) are views showing a general configuration of an ultrasonic testing apparatus in accordance with a second modification of the present invention, which includes a nozzle for spraying purge air, and one example of the results of detection of artificial flaws formed on the outer surface of an end portion of pipe made by using the ultrasonic testing apparatus in accordance with the second modification, FIG. 8A being a sectional front view showing a general configuration of the ultrasonic testing apparatus, FIG. 8B being a diagram showing a testing signal obtained by an ultrasonic probe for detecting lamination when the pipe with the artificial flaws formed thereon is rotated in the circumferential direction without being relatively moved in the axial direction, and the purge air is not sprayed from the nozzle shown in FIG. 8A, and FIG. 8C being a diagram showing a testing signal obtained by the ultrasonic probe for detecting lamination when the pipe with the artificial flaws formed thereon is rotated in the circumferential direction without being relatively moved in the axial direction, and the purge air is sprayed from the nozzle shown in FIG. 8A.
Figure 8B:
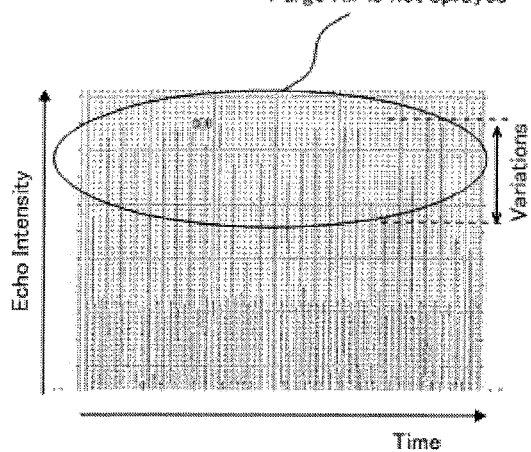
Figure 8C:
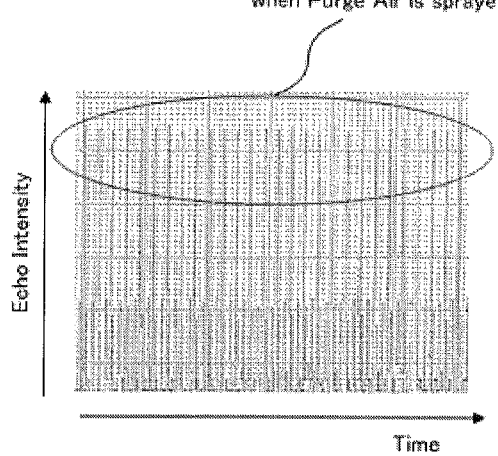

FIG. 8A, FIG. 8B, and FIG. 8C are views showing a general configuration of an ultrasonic testing apparatus in accordance with a second modification of this embodiment, which includes the nozzle for spraying purge air, and one example of the results of detection of artificial flaws formed on the outer surface of an end portion of pipe made by using the ultrasonic testing apparatus in accordance with the second modification. FIG. 8A is a sectional front view showing a general configuration of the ultrasonic testing apparatus, FIG. 8B is a diagram showing a testing signal obtained by the ultrasonic probe 1A when the pipe with the artificial flaws formed thereon is rotated in the circumferential direction without being relatively moved in the axial direction, and the purge air is not sprayed from the nozzle shown in FIG. 8A, and FIG. 8C is a diagram showing a testing signal obtained by the ultrasonic probe 1A when the pipe with the artificial flaws formed thereon is rotated in the circumferential direction without being relatively moved in the axial direction, and the purge air is sprayed from the nozzle shown in FIG. 8A.

As shown in FIG. 8A, an ultrasonic testing apparatus 100B in accordance with the second modification includes a nozzle 7 for spraying purge air A in addition to the configuration of the above-described ultrasonic testing apparatus 100. The nozzle 7 is positioned so that the purge air is sprayed toward a portion on the outer surface of the pipe P that is located on the upstream side in the direction of rotation of the pipe P with respect to a portion on the outer surface of the pipe P, which is in contact with the coupling medium (specifically, the film W2 of coupling medium) staying in the coupling medium reserver part, the portion on the outer surface of the pipe P being located in a range not larger than 180 degrees in the circumferential direction of the pipe P with respect to the lowest portion P1 of the pipe P ($\theta \leq 180°$ in FIG. 8A). The nozzle 7 is installed on a stage (not shown) moving vertically. By drivingly controlling this stage according to the outside diameter of the pipe P, the vertical position of the nozzle 7 is adjusted automatically so that the angle $\theta$ is substantially constant regardless of the outside diameter of the pipe P.

According to the ultrasonic testing apparatus 100B in accordance with this modification, the coupling medium W drawn onto the outer surface of the pipe P, while rotating together with the pipe P and entraining air bubbles, is purged from the outer surface of the pipe P by the purge air A sprayed from the nozzle 7, which reduces possibility of the coupling medium W involving the air bubbles again intruding into the film W2 of coupling medium. Therefore, possibility of reduced testing accuracy due to the air bubbles staying in the film W2 of coupling medium can be reduced. Specifically, when the purge air A is not sprayed from the nozzle 7 (FIG. 8B), the variations in echoes from the artificial flaws are increased by the influence of the air bubbles staying in the film W2 of coupling medium, and on the other hand, when the purge air A is sprayed from the nozzle 7 (FIG. 8C), the variations in echoes from the artificial flaws are small, so that stable pipe testing can be performed.

Needless to say, a configuration in which the above-described ultrasonic testing apparatus 100A in accordance with the first modification and ultrasonic testing apparatus 100B in accordance with the second modification are combined with each other (that is, a configuration including the pre-immersing device 4, the control unit 5, the pipe end detecting sensor 6, and the nozzle 7 in addition to the configuration of the ultrasonic testing apparatus 100) is also available.

The initial position of the probe holder 2 that the above-described ultrasonic testing apparatus 100 in accordance with the this embodiment, ultrasonic testing apparatus 100A in accordance with the first modification, and ultrasonic testing apparatus 100B in accordance with the second modification have is preferably set as described below.

Setting of Initial Position in Vertical Direction

Figure 9A:
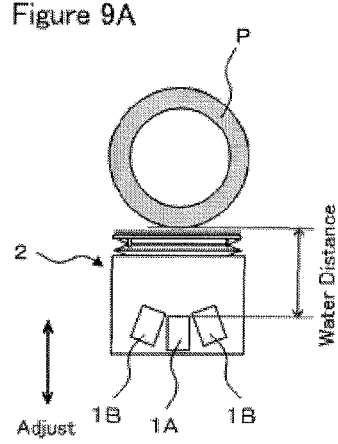
FIG. 9 (FIG. 9A and FIG. 9B) are views showing a method of setting the initial position in the vertical direction of a probe holder, FIG. 9A being a schematic view showing a state in which the initial position in the vertical direction of the probe holder is set, and FIG. 9B being a schematic diagram of an A scope display of testing signal obtained in the state shown in FIG. 9A.
Figure 9B:
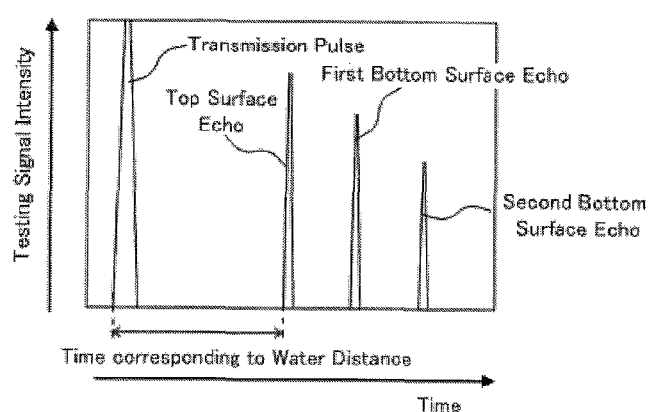

FIG. 9A and FIG. 9B are views showing a method of setting the initial position in the vertical direction of the probe holder. FIG. 9A is a schematic view showing a state in which the initial position in the vertical direction of the probe holder is set, and FIG. 9B is a schematic diagram of an A scope display of testing signal obtained in the state shown in FIG. 9A.

In setting the initial position in the vertical direction of the probe holder 2, a pipe P that has a cross section as close as possible to a complete round and is less bent is prepared. Next, regarding the position along the axial direction of this pipe P, the probe holder 2 is set, for example, at the pipe testing start position (refer to FIG. 7B), and the testing signal obtained by the ultrasonic probe 1A is displayed on the A scope in the state in which the probe holder 2 does not follow the pipe P and in the state in which the pipe P is at rest (FIG. 9B). Then, the relative position in the vertical direction of the probe holder 2 with respect to the pipe P is adjusted so that the distance (water distance) between the ultrasonic probe 1A and the pipe P, which is determined by the A scope, coincides with a target value (FIG. 9A). Specifically, the relative position in the vertical direction of the probe holder 2 with respect to the pipe P is adjusted so that the water distance determined by multiplying the time from when a transmission pulse appears to when a surface echo appears on the A scope shown in FIG. 9B by the sound velocity in the coupling medium W coincides with the target value. The relative position in the vertical direction of the probe holder 2 is adjusted, for example, by moving a moving mechanism provided in the follow-up device in the vertical direction at a 0.1 mm pitch.

According to the above-described setting method, the testing signal obtained by the ultrasonic probe 1A is displayed on the A scope, and the relative position in the vertical direction of the probe holder 2 with respect to the pipe P is adjusted so that the water distance determined by the A scope coincides with the target value. Thereby, the initial position in the vertical direction of the ultrasonic probe 1A, and in turn, the initial positions in the vertical direction of the paired ultrasonic probes 1B can be set easily and accurately.

Setting of Initial Position in Horizontal Direction

Figure 10A:
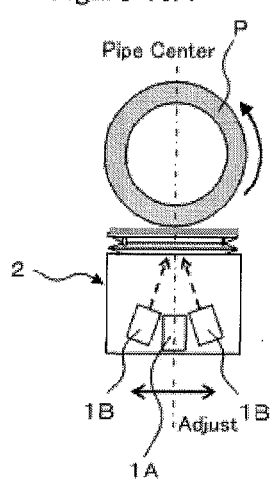
FIG. 10 (FIG. 10A, FIG. 10B, FIG. 10C, FIG. 10D, and FIG. 10E) are views showing a method of setting the initial position in the horizontal direction of a probe holder, FIG. 10A being a schematic view showing a state in which the initial position in the horizontal direction of the probe holder is set, FIG. 10B being a diagram showing one example of a testing signal obtained by one ultrasonic probe for detecting axial flaws when artificial flaws (axial flaws) are formed on the outer surface of an end portion of a pipe, and the pipe is rotated in the circumferential direction while being relatively moved in the axial direction in a state in which the probe holder shifts −0.4 mm in the horizontal direction from the center position of the pipe shown in FIG. 10A, FIG. 10C being a diagram showing one example of a testing signal obtained by the other ultrasonic probe for detecting axial flaws in the same state as that in FIG. 10B, FIG. 10D being a diagram showing one example of a testing signal obtained by one ultrasonic probe for detecting axial flaws when the pipe is rotated in the circumferential direction while being relatively moved in the axial direction after the position of probe holder in the state shown in FIG. 10B has been adjusted by +0.4 mm in the horizontal direction, and FIG. 10E being a diagram showing one example of a testing signal obtained by the other ultrasonic probe for detecting axial flaws in the same state as that in FIG. 10D.
Figure 10B:
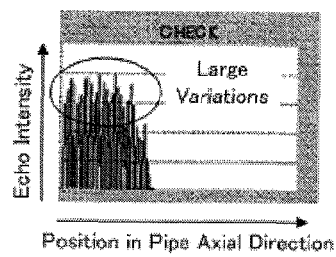
Figure 10C:
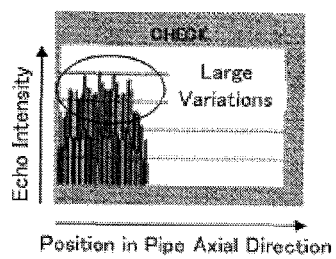
Figure 10D:
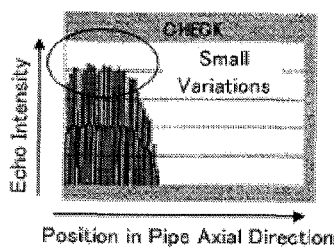
Figure 10E:
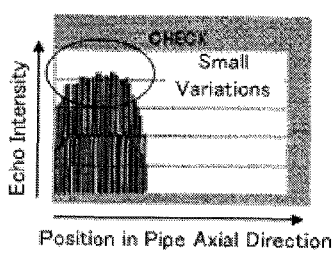

FIG. 10A, FIG. 10B, FIG. 10C, FIG. 10D, and FIG. 10E are views showing a method of setting the initial position in the horizontal direction of the probe holder. FIG. 10A is a schematic view showing a state in which the initial position in the horizontal direction of the probe holder is set. FIG. 10B is a diagram showing one example of the testing signal obtained by one ultrasonic probe 1B when artificial flaws (axial flaws) are formed on the outer surface of an end portion of the pipe P, and the pipe P is rotated in the circumferential direction while being relatively moved in the axial direction in the state in which the probe holder 2 shifts (the ultrasonic probe 1A shifts) −0.4 mm in the horizontal direction from the center position of the pipe shown in FIG. 10A (0.4 mm to the left-hand side on the paper of FIG. 10A from the center position of pipe). FIG. 10C is a diagram showing one example of the testing signal obtained by the other ultrasonic probe 1B in the same state as that in FIG. 10B. FIG. 10D is a diagram showing one example of the testing signal obtained by one ultrasonic probe 1B when the pipe P is rotated in the circumferential direction while being relatively moved in the axial direction after the position of probe holder 2 in the state shown in FIG. 10B has been adjusted by +0.4 mm in the horizontal direction (0.4 mm to the right-hand side on the paper of FIG. 10A). FIG. 10E is a diagram showing one example of the testing signal obtained by the other ultrasonic probe 1B in the same state as that in FIG. 10D.

In setting the initial position in the horizontal direction of the probe holder 2 as well, a pipe P that has a cross section as close as possible to a complete round and is less bent is prepared (the same pipe as the pipe P used in setting the initial position in the vertical direction of the probe holder 2 may be used). Next, regarding the position along the axial direction of this pipe P, the probe holder 2 is set, for example, at the pipe testing start position (refer to FIG. 7B). In the portion of the pipe P facing the probe holder 2, artificial flaws (axial flaws) are formed in advance. Then, the relative position in the horizontal direction of the probe holder 2 with respect to the pipe P (the horizontal direction intersecting at right angles to the axial direction of the pipe P) is adjusted so that in the state in which the probe holder 2 does not follow the pipe P, when the pipe P is rotated in the circumferential direction (in the example shown in FIG. 10A, FIG. 10B, FIG. 10C, FIG. 10D, and FIG. 10E, the pipe P is also moved relatively in the axial direction), the intensities of flaw signals (echo intensities from the artificial flaws) obtained by the paired ultrasonic probes 1B each fall within a fixed range (for example, within the range of about ±1 dB of the average value of flaw signal intensities) (FIG. 10A). Specifically, as shown in FIGS. 10B and 10C, and in the case where the variations in flaw signal intensities are large, as shown in FIGS. 10D and 10E, the relative position in the horizontal direction of the probe holder 2 is adjusted until the variations in flaw signal intensities become small. The relative position in the horizontal direction of the probe holder 2 is adjusted, for example, by moving a moving mechanism provided in the follow-up device in the horizontal direction at a 0.1 mm pitch.

In the example shown in FIG. 10A, FIG. 10B, FIG. 10C, FIG. 10D, and FIG. 10E, since the pipe P is relatively moved in the axial direction (therefore, the artificial flaws are also relatively moved in the axial direction of the pipe P), in the end portion in the longitudinal direction of the artificial flaw, the ratio of the ultrasonic waves applied to the artificial flaw to the ultrasonic waves transmitted from the ultrasonic probes 1B decreases. In FIGS. 10B to 10D, the testing signals in a portion that is not encircled correspond to a portion in which the ratio of the ultrasonic waves applied to the artificial flaws decreases, so that those testing signals may be ignored in evaluating the variations in flaw signal intensities.

If the probe holder 2 shifts in the horizontal direction from the center position of the pipe P, as a reason for the increase in variations in flaw signal intensities obtained by the paired ultrasonic probes 1B, the reasons described in the items (1) and (2) below are conceivable.

(1) The contact state between the film W2 of coupling medium and the pipe P in the vicinity of the incident point of ultrasonic waves transmitted from the paired ultrasonic probes 1B to the pipe P (in the vicinity of the center position of the spacer 23) is stabilized most (the acoustic coupling state becomes the best) when the probe holder 2 is located at the center position of the pipe P (when the center position of the spacer 23 coincides with the center position of the pipe P). Therefore, when the probe holder 2 is located at the center position of the pipe P, the ultrasonic waves transmitted from the paired ultrasonic probes 1B are stably applied to the pipe P. In contrast, if the probe holder 2 shifts in the horizontal direction from the center position of the pipe P, the vertical gap between the upper surface of the spacer 23 and the pipe P varies greatly depending on places in the vicinity of the center position of the spacer 23 (in the vicinity of the incident point of ultrasonic waves), so that the contact state between the film W2 of coupling medium and the pipe P is liable to become unstable (the acoustic coupling state is liable to become unstable). Therefore, the ultrasonic waves transmitted from the paired ultrasonic probes 1B are not stably applied to the pipe P, so that it is conceivable that the variations in flaw signal intensities become large.

(2) Generally, in the case where the pipe P is tested at an oblique angle, the incident angle of ultrasonic waves to the pipe P is set in a predetermined angle range in which the sound pressure of ultrasonic waves is stable (hereinafter refer to as a sound pressure stabilizing angle range). For example, in the case where a steel pipe is tested at an oblique angle with water being used as the coupling medium W, the sound pressure of ultrasonic waves stabilizes most in the vicinity of an 18° incident angle of ultrasonic waves to the steel pipe, so that the incident angle is set at about 18°±2°. If the ultrasonic waves are applied to the pipe P at an incident angle exceeding this sound pressure stabilizing angle range, the sound pressure of ultrasonic waves changes greatly with a slight change in incident angle (the dependence on angle of the sound pressure increases). If the probe holder 2 shifts in the horizontal direction from the center position of the pipe P, the incident angle of the ultrasonic waves transmitted from the paired ultrasonic probes 1B to the pipe P shifts, and may exceed the sound pressure stabilizing angle range. If a minute follow-up error occurs on the probe holder 2 (therefore, the incident angle of the ultrasonic waves transmitted from the paired ultrasonic probes 1B changes slightly) in the state in which the incident angle of the ultrasonic waves transmitted from the paired ultrasonic probes 1B to the pipe P exceeds the sound pressure stabilizing angle range, it is conceivable that the variations in flaw signal intensities become large as the result of a great change in sound pressure of ultrasonic waves.

According to the above-described setting method, the relative position in the horizontal direction of the probe holder 2 with respect to the pipe P is adjusted so that when the pipe P is rotated in the circumferential direction, the flaw signal intensities obtained by the paired ultrasonic probes 1B each fall within a fixed range, whereby the initial positions in the horizontal direction of the paired ultrasonic probes 1B, and in turn, the initial position in the horizontal direction of the ultrasonic probe 1A can be set easily and accurately.

The invention claimed is:

1. An ultrasonic testing apparatus for a pipe or tube end portion, comprising:
   an ultrasonic probe which is disposed under the end portion of a pipe or tube laid in the horizontal direction to face the pipe or tube end portion, the ultrasonic probe transmitting ultrasonic waves to the end portion of the pipe or tube and receiving the ultrasonic waves therefrom; and
   a probe holder housing the ultrasonic probe which is disposed under the end portion of the pipe or tube to face the pipe or tube end portion and following the pipe or tube rotating in a circumferential direction,
   the probe holder comprising a coupling medium reserver part which surrounds a space between the ultrasonic probe and the end portion of the pipe or tube to contain a coupling medium therein, and
   the coupling medium reserver part comprising:
   a coupling medium reserver part body into which the coupling medium is supplied;
   an annular bellows part which is attached to an upper side of the coupling medium reserver part body so as to internally communicate with the coupling medium reserver part body, and can expand and contract vertically, the coupling medium supplied to the coupling medium reserver part flowing into the annular bellows part; and
   an annular spacer which is attached to the upper side of the bellows part, and at least an upper surface of the annular spacer being a flat horizontal surface, the coupling medium flowing from the annular bellows part to the annular spacer, and a film in contact with the pipe or tube end portion being formed by the coupling medium raised beyond the upper surface of the annular spacer, wherein
   the coupling medium reserver part body comprises a coupling medium supply port for supplying the coupling medium into the coupling medium reserver part body and a coupling medium spraying nozzle configured for spraying the coupling medium toward the ultrasonic transmitting/receiving surface of an ultrasonic probe.

2. The ultrasonic testing apparatus for a pipe or tube end portion according to claim 1, wherein the coupling medium reserver part further comprises a tubular member which is attached to a lower surface of the spacer and is fitted in the bellows part.

3. The ultrasonic testing apparatus for a pipe or tube end portion according to claim 1, wherein the coupling medium reserver part body is provided with the coupling medium supply port for supplying the coupling medium in a tangential direction of a predetermined arc around a vertical center axis, and a coupling medium discharge port for discharging the coupling medium in the tangential direction of the arc.

4. The ultrasonic testing apparatus for a pipe or tube end portion according to claim 1, wherein
   the ultrasonic testing apparatus further comprises a pre-immersing device installed on the probe holder and a control unit; and
   the control unit reciprocates the probe holder relative to the pipe or tube along the axial direction of the pipe or tube rotating in the circumferential direction, sprays the coupling medium from the pre-immersing device toward the pipe or tube when the probe holder moves forward in the pipe or tube testing range of the pipe or tube end portion, and stops the spraying of coupling medium from the pre-immersing device when the ultrasonic testing is performed while the probe holder moves backward in the pipe or tube testing range of the pipe or tube end portion.

5. The ultrasonic testing apparatus for a pipe or tube end portion according to claim 4, wherein
the coupling medium reserver part body comprises the coupling medium spraying nozzle for spraying the coupling medium toward the ultrasonic transmitting/receiving surface of the ultrasonic probe; and
the control unit sprays the coupling medium from the coupling medium spraying nozzle toward the ultrasonic transmitting/receiving surface of the ultrasonic probe when the probe holder moves forward in the pipe or tube testing range of the pipe or tube end portion, and stops the spraying of coupling medium from the coupling medium spraying nozzle when the ultrasonic testing is performed while the probe holder moves backward in the pipe or tube testing range of the pipe or tube end portion.

6. The ultrasonic testing apparatus for a pipe or tube end portion according to claim 1, wherein the ultrasonic testing apparatus further comprises a nozzle for spraying purge air toward a portion on an outer surface of the pipe or tube which is located on the upstream side in the direction of rotation of the pipe or tube with respect to a portion on the outer surface of the pipe or tube, which is in contact with the coupling medium staying in the coupling medium reserver part, the portion on the outer surface of the pipe or tube being located in a range not larger than 180 degrees in the circumferential direction of the pipe or tube with respect to a lowest portion of the pipe or tube.

7. A method of setting the initial position of a probe holder which the ultrasonic testing apparatus according to claim 1 has, wherein
the ultrasonic probe comprising a first ultrasonic probe and a pair of second ultrasonic probes; the probe holder houses the first ultrasonic probe for propagating ultrasonic waves in the wall thickness direction of the pipe or tube and the pair of second ultrasonic probes disposed with the first ultrasonic probe being held therebetween to propagate ultrasonic waves in the circumferential direction of the pipe or tube, the first ultrasonic probe and the pair of second ultrasonic probes being positioned, at the initial position of the probe holder, in the probe holder so that the incident points of ultrasonic waves transmitted from the first ultrasonic probe and the pair of second ultrasonic probes to the pipe or tube substantially coincide with each other; and
the method comprises:
a step of adjusting the relative position in a vertical direction of the probe holder with respect to the pipe or tube so that in the state in which the probe holder does not follow the pipe or tube, a testing signal obtained by the first ultrasonic probe is displayed on an A scope, and the distance between the first ultrasonic probe and the pipe or tube which is determined by the A scope coincides with a target value, and
a step of forming artificial flaws extending in the pipe or tube axial direction in a pipe end portion, and of adjusting the relative position in the horizontal direction intersecting at right angles to the pipe or tube axial direction of the probe holder with respect to the pipe or tube so that in the state in which the probe holder does not follow the pipe or tube, when the pipe or tube is rotated in the circumferential direction, the flaw signal intensities obtained by the pair of second ultrasonic probes each fall within a fixed range.

* * * * *